United States Patent
Ebenezer

(10) Patent No.: US 11,847,200 B2
(45) Date of Patent: Dec. 19, 2023

(54) METHODS AND APPARATUS FOR SYSTEM IDENTIFICATION

(71) Applicant: Cirrus Logic International Semiconductor Ltd., Edinburgh (GB)

(72) Inventor: Samuel P. Ebenezer, Gilbert, AZ (US)

(73) Assignee: Cirrus Logic Inc., Austin, TX (US)

( * ) Notice: Subject to any disclaimer, the term of this patent is extended or adjusted under 35 U.S.C. 154(b) by 0 days.

(21) Appl. No.: 17/706,982

(22) Filed: Mar. 29, 2022

(65) Prior Publication Data
US 2023/0315823 A1    Oct. 5, 2023

(51) Int. Cl.
| | |
|---|---|
| *A61B 5/117* | (2016.01) |
| *G06F 21/32* | (2013.01) |
| *G10K 11/178* | (2006.01) |
| *G10L 25/51* | (2013.01) |
| *A61B 5/12* | (2006.01) |

(52) U.S. Cl.
CPC ............ *G06F 21/32* (2013.01); *A61B 5/117* (2013.01); *A61B 5/12* (2013.01); *G10K 11/17817* (2018.01); *G10K 11/17825* (2018.01); *G10K 11/17854* (2018.01); *G10L 25/51* (2013.01); *G10K 2210/1081* (2013.01); *G10K 2210/3028* (2013.01); *G10K 2210/3035* (2013.01)

(58) Field of Classification Search
CPC ........... G06F 21/32; G06F 21/31; G07C 9/37; A61B 5/117; A61B 5/1171; H04R 1/1041; H04L 63/0861
See application file for complete search history.

(56) References Cited

U.S. PATENT DOCUMENTS

| | | | |
|---|---|---|---|
| 8,187,202 B2 | 5/2012 | Akkermans et al. | |
| 10,867,019 B2 | 12/2020 | Yano et al. | |
| 2002/0198690 A1* | 12/2002 | Holzrichter | G01H 9/00 703/2 |
| 2008/0262382 A1* | 10/2008 | Akkermans | G07C 9/37 600/559 |
| 2012/0215519 A1* | 8/2012 | Park | H04R 3/005 381/17 |
| 2012/0310640 A1* | 12/2012 | Kwatra | G10K 11/17854 381/71.1 |
| 2020/0342246 A1* | 10/2020 | Harvey | G06V 40/10 |
| 2021/0248403 A1 | 8/2021 | Harvey et al. | |

FOREIGN PATENT DOCUMENTS

WO    2006054205 A1    5/2006

OTHER PUBLICATIONS

Combined Search and Examination Report under Sections 17 and 18(3), UKIPO, Application No. GB2302129.8, dated Jul. 26, 2023.

* cited by examiner

*Primary Examiner* — Kile O Blair
(74) *Attorney, Agent, or Firm* — Jackson Walker L.L.P

(57) ABSTRACT

A method of identifying a system, the method comprising: obtaining an indication of background noise present at the system; generating a probe signal based on the indication; applying the probe signal to the system; estimating a response of the system to the probe signal; and identifying the system based on the measured response and the probe signal, wherein the probe signal comprises a whitening component configured to whiten noise in the estimated response due to the background noise present at the system.

26 Claims, 13 Drawing Sheets

METHODS AND APPARATUS FOR SYSTEM IDENTIFICATION

TECHNICAL FIELD

Embodiments of the present disclosure relate to methods, apparatus and systems for system identification, for example for biometric processes.

BACKGROUND

It is known that the acoustic properties of a user's ear, whether the outer parts (known as the pinna or auricle), the ear canal or both, differ substantially between individuals and can therefore be used as a biometric to identify the user. One or more loudspeakers or similar transducers positioned close to or within the ear generate an acoustic stimulus, and one or more microphones or other transducers similarly positioned close to or within the ear detect the acoustic response of the ear to the acoustic stimulus. The response may be an ear canal impulse response (ECIR) or an ear canal frequency response (ECFR). One or more features may be extracted from the response signal and used to characterize an individual.

For example, the ear canal is a resonant system, and therefore one feature which may be extracted from the response signal is the impulse response or frequency response of the ear canal (ECIR or ECFR). If the measured resonant frequency (i.e. in the response signal) differs from a stored resonant frequency for the user, a biometric algorithm coupled to receive and analyse the response signal may return a negative result. Other features of the response signal may be similarly extracted and used to characterize the individual. For example, the features may comprise one or more mel frequency cepstrum coefficients. More generally, the transfer function between the acoustic stimulus and the measured response signal (or features of the transfer function) may be determined and compared to a stored transfer function (or stored features of the transfer function) which is characteristic of the user.

One problem associated with ear biometric systems is that the signal to noise ratio of the measured response signal is typically quite low as the biometric features of the signal are relatively weak. This problem can be exacerbated depending on a number of factors. For example, the user may be present in a noisy environment. For example, earphones used to acquire the ear biometric data may be poorly fitted to the user's ear (e.g. inserted too far into the user's ear, or not sufficiently inserted). For example, the user may be generating noise in the canal or headset due to the user's own voice, chewing sounds and handling of the headset. To improve signal-to-noise ratio (SNR) and to ensure as many frequency modes as possible of ear canals of a population group are excited, probe signals for biometrics typically comprise white noise. However, white noise tends to be perceptually unpleasant to the human ear. SNR may also be improved by increasing the level of the probe signal. However, high level probe signals tend to be intrusive and harsh to the human ear.

Ear canal characterisation can also be key to adaptive active noise cancellation (ANC) systems. ANC performance depends on the accurate estimation of ear canal response. The accuracy of the estimation in high-level background noise conditions can be improved by appropriate selection of the playback signal used to stimulate the ear canal system.

SUMMARY

According to a first aspect of the disclosure, there is provided a method of identifying a system, the method comprising: obtaining an indication of background noise present at the system; generating a probe signal based on the indication; applying the probe signal to the system; estimating a response of the system to the probe signal; and identifying the system based on the measured response and the probe signal, wherein the probe signal comprises a whitening component configured to whiten noise in the estimated response due to the background noise present at the system.

The probe signal may be an acoustic stimulus for use in an acoustic process on a user and the system comprises an ear canal of the user. The acoustic process may comprise active noise cancellation (ANC). The probe signal may be an audio playback signal.

The estimated response may represent a combination of a leakage path around a personal audio device worn by the user and a response of the ear canal to probe signal. For example, the leakage path may be an acoustic path between the inside of the ear canal and the outside of the ear due to poor occlusion of the ear by the personal audio device. Gaps between the ear or head and the personal audio device may allow sound to travel between the ear canal and the outside of the ear canal. Such an acoustic path may affect ANC and thus be used to adapt the probe signal for ANC. Additionally, the ear canal response may also affect ANC. Thus, by estimating a response to the probe signal which takes into account the leakage path in addition to the ear canal impulse response, an improved estimation of ANC parameters may be achieved.

To that end, the estimated response may be used to adapt the probe signal for the ANC. The ANC may comprise feedback ANC or feedforward ANC or a combination of both feedback ANC and feedforward ANC. Feedback and feedforward ANC are described in more detail below.

In some embodiments, the acoustic process comprises an ear biometric process. In which case, identifying the system may comprise obtaining an ear canal response of the user's ear. The indication of background noise may be obtained from an internal microphone of a personal audio device proximate the user's ear. The internal microphone may be used to pick up environmental noise which has reached the ear canal despite the personal audio device. The indication of background noise may be obtained from signals received from both the internal microphone and an external microphone of the personal audio device worn by the user. For example, obtaining the indication of background noise may comprise comparing an internal microphone signal from the internal microphone to an external microphone signal at the external microphone.

In some embodiments, obtaining the indication of background noise may comprise estimating a transfer function between the external microphone signal and internal microphone signal, and filtering the external microphone signal by the estimated transfer function.

Generating the probe signal may comprise adapting a fixed probe signal based on the indication of background noise. For example, generating the probe signal may comprise determining filter parameters for whitening the noise in the measured response due to the background noise present at the system; and filtering the fixed probe signal using the filter parameters.

Identifying the system may comprise performing parametric modelling on the estimated response to generate a parametric representation of the estimated response. The parametric modelling may comprise linear predictive coding (LPC).

Identifying the system may comprise estimating a frequency spectrum of the system response based on parametric representation, and comparing one or more features of the frequency spectrum with one or more templates.

Identifying the system may comprise generating an authentication result for each comparison between the one or more features and the one or more templates. The authentication result may be generated by a machine learning classifier trained using the one or more templates.

The method may further comprise comparing the measured response or the frequency spectrum with the one or more templates.

According to another aspect of the disclosure, there is provided a method of authenticating a user as an authorised user, the method comprising: obtaining an indication of background noise present at an ear canal of the user; generating a probe signal based on the indication; applying the probe signal to the ear canal of the user; measuring sound proximate the ear canal during or after application of the probe signal; estimating a response of the ear canal to the probe signal based on the measured sound; and identifying the user based on the estimated response and the probe signal, wherein the probe signal comprises a whitening component configured to whiten the noise present in the estimated response due to the background noise present at the system.

According to another aspect of the disclosure, there is provided a non-transitory machine-readable medium storing instructions which, when executed by one or more processors, cause an electronic apparatus to perform the method as described above.

According to another aspect of the disclosure, there is provided an apparatus for identifying a system, the apparatus comprising: an input for obtaining an indication of background noise present at the system; and one or more processors configured to control the apparatus to: generate a probe signal based on the indication; apply the probe signal to the system; estimate a response of the system to the probe signal; and identify the system based on the measured response and the probe signal, wherein the probe signal comprises a whitening component configured to whiten noise in the estimated response due to the background noise present at the system.

According to another aspect of the disclosure, there is provided an apparatus for identifying a user, the apparatus comprising: an input for obtaining an indication of background noise present at an ear canal of the user; and one or more processors configured to control the apparatus to: generate a probe signal based on the indication; apply the probe signal to the ear canal of the user; measure sound proximate the ear canal during or after application of the probe signal; estimate a response of the ear canal to the probe signal based on the measured sound; and identify the user based on the estimated response and the probe signal, wherein the probe signal comprises a whitening component configured to whiten the noise present in the estimated response due to the background noise present at the system.

According to another aspect of the disclosure, there is provided an apparatus or identifying a user, the apparatus comprising: an input for obtaining an indication of background noise present at an ear canal of the user; and one or more processors configured to control the apparatus to perform any of the methods described above.

According to another aspect of the disclosure, there is provided an electronic device comprising one or more of the apparatuses described above.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the disclosure relate to methods, apparatus and systems for biometric processes, and particularly to methods, apparatus and systems for improving biometric processes involving the measured response of a user's ear to an acoustic stimulus.

Figure 1A:
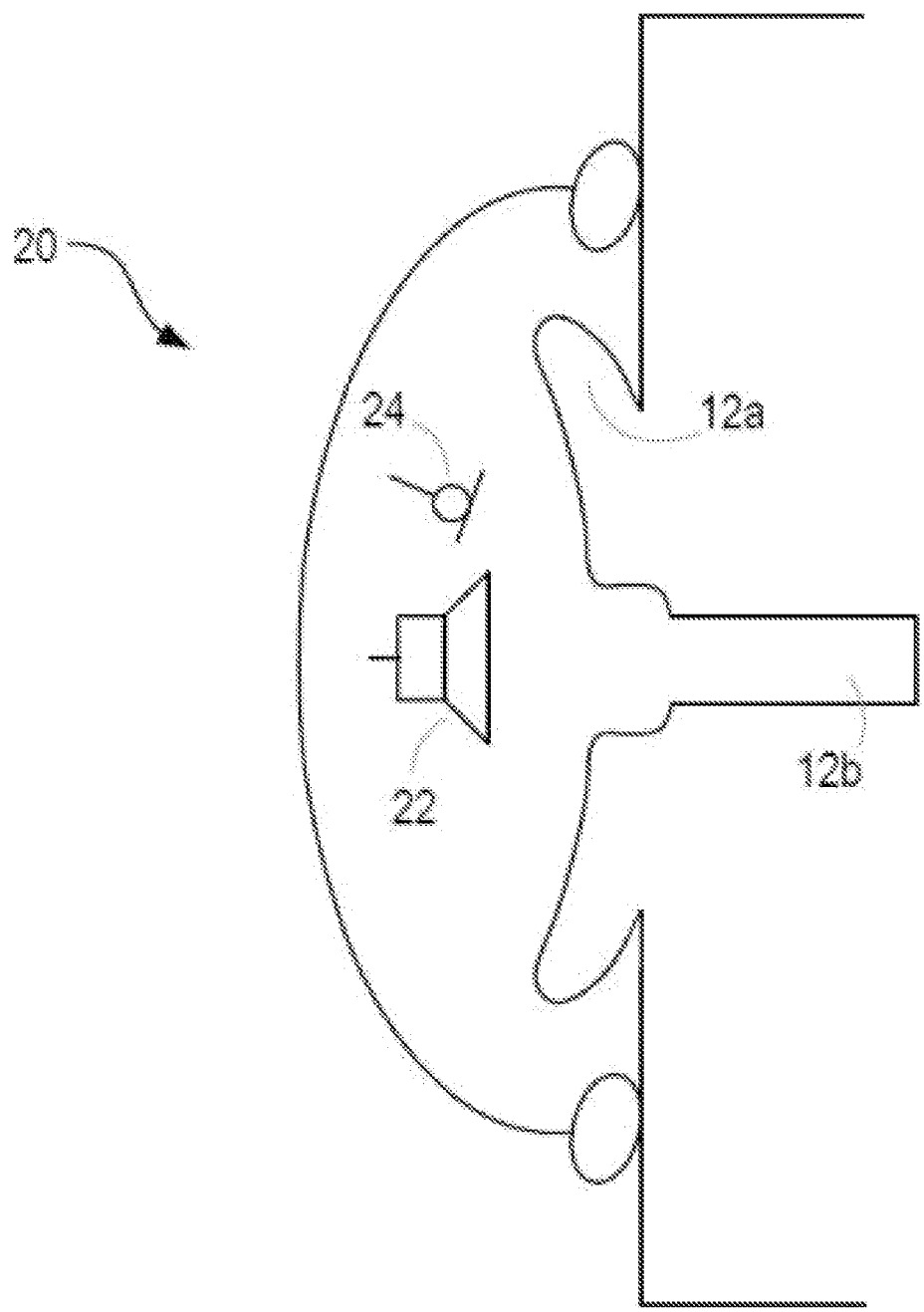
FIGS. 1a to 1e show examples of personal audio devices.

FIG. 1a shows a schematic diagram of a user's ear, comprising the (external) pinna or auricle 12a, and the (internal) ear canal 12b. A personal audio device 20 comprising a circum-aural headphone is worn by the user over the ear. The headphone comprises a shell which substantially surrounds and encloses the auricle 12a, so as to provide a physical barrier between the user's ear and the external environment. Cushioning or padding may be provided at an edge of the shell, so as to increase the comfort of the user, and also the acoustic coupling between the headphone and the user's skin (i.e. to provide a more effective barrier between the external environment and the user's ear).

The headphone comprises one or more loudspeakers 22 positioned on an internal surface of the headphone and arranged to generate acoustic signals towards the user's ear and particularly the ear canal 12b. The headphone further comprises one or more microphones 24, also positioned on the internal surface of the headphone, arranged to detect acoustic signals within the internal volume defined by the headphone, the auricle 12a and the ear canal 12b.

The headphone may be able to perform active noise cancellation, to reduce the amount of noise experienced by the user of the headphone. Active noise cancellation operates by detecting a noise (i.e. with a microphone) and generating a signal (i.e. with a loudspeaker) that has the same amplitude as the noise signal but is opposite in phase. The generated signal thus interferes destructively with the noise and so lessens the noise experienced by the user.

Active noise cancellation may operate on the basis of feedback signals, feedforward signals, or a combination of both. Feedforward active noise cancellation utilizes one or more microphones on an external surface of the headphone, operative to detect the environmental noise before it reaches the user's ear. The detected noise is processed quickly, and the cancellation signal is generated so as to match the incoming noise as it arrives at the user's ear. Feedback active noise cancellation utilizes one or more error microphones positioned on the internal surface of the headphone, operative to detect the combination of the noise and the audio playback signal generated by the one or more loudspeakers. This combination is used in a feedback loop, together with knowledge of the audio playback signal, to adjust the cancelling signal generated by the loudspeaker and so reduce the noise. The microphone 24 shown in FIG. 1a may therefore form part of an active noise cancellation system, for example, as an error microphone. Adaptive ANC systems require estimation of the ear canal response system (sometimes referred to as a secondary path). The secondary path response (the ear canal response system for the purpose of ANC) is a function of both the physiological structure of ear canal and the quality of fit of the headset implementing ANC. The playback signal can be adaptively modified based on the prevailing noise conditions.

Figure 1B:
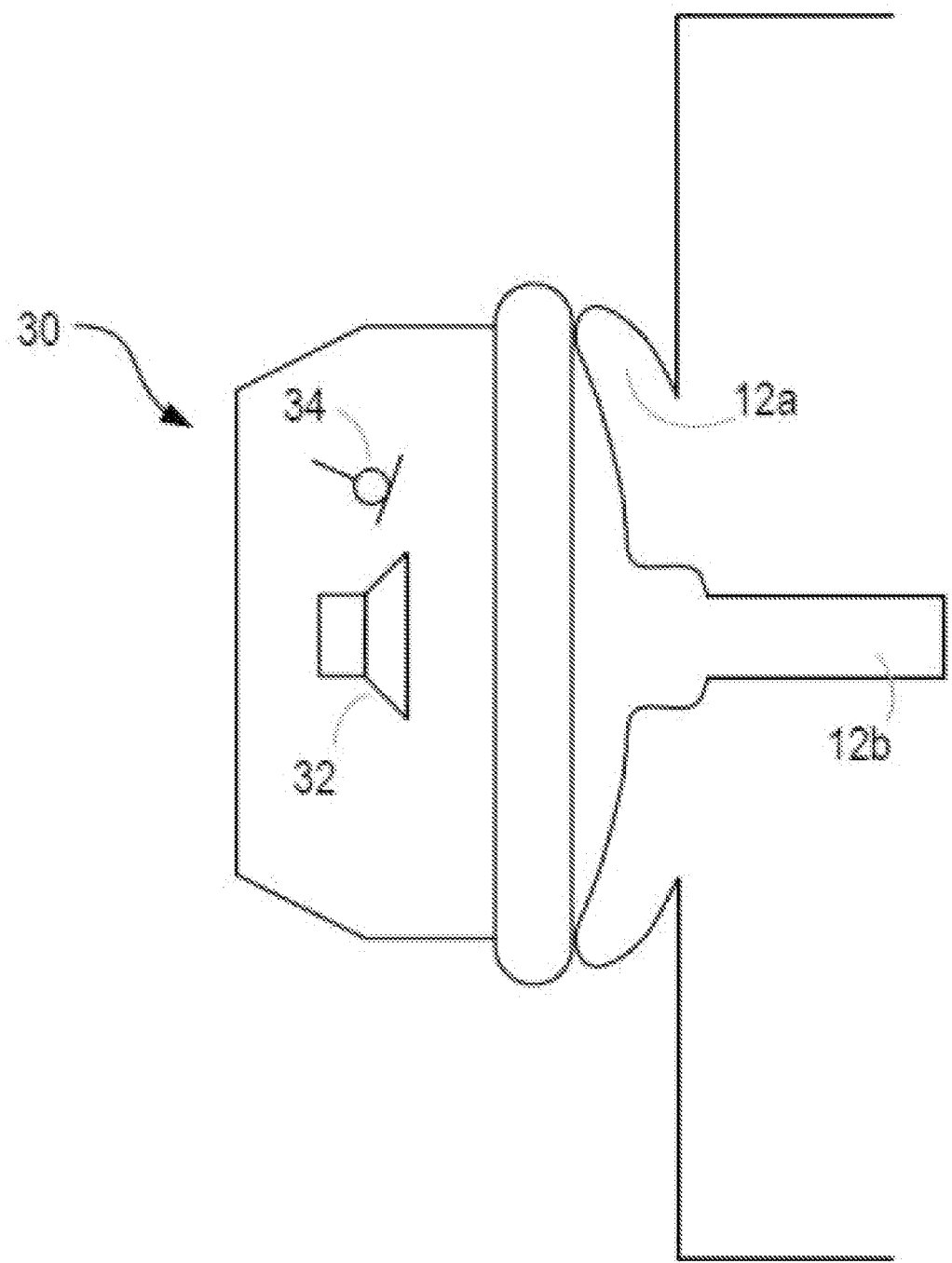

FIG. 1b shows an alternative personal audio device 30, comprising a supra-aural headphone. The supra-aural headphone does not surround or enclose the user's ear, but rather sits on the auricle 12a. The headphone may comprise a cushion or padding to lessen the impact of environmental noise. As with the circum-aural headphone shown in FIG. 1a, the supra-aural headphone comprises one or more loudspeakers 32 and one or more microphones 34. The loudspeaker(s) 32 and the microphone(s) 34 may form part of an active noise cancellation system, with the microphone 34 serving as an error microphone.

Figure 1C:
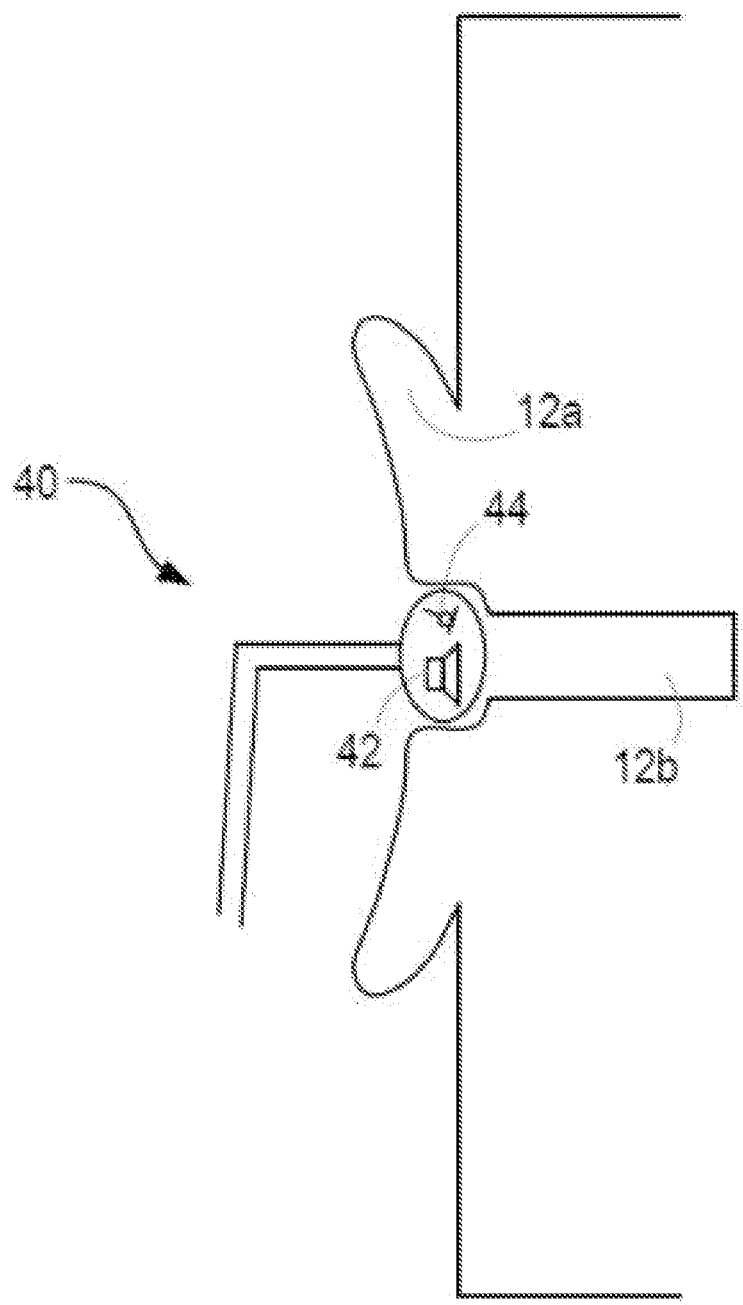

FIG. 1c shows a further alternative personal audio device 40, comprising an intra-concha headphone (or earphone). In use, the intra-concha headphone sits inside the user's concha cavity. The intra-concha headphone may fit loosely within the cavity, allowing the flow of air into and out of the user's ear canal 12b.

As with the devices shown in FIGS. 1a and 1b, the intra-concha headphone comprises one or more loudspeakers 42 and one or more microphones 44, which may form part of an active noise cancellation system.

Figure 1D:
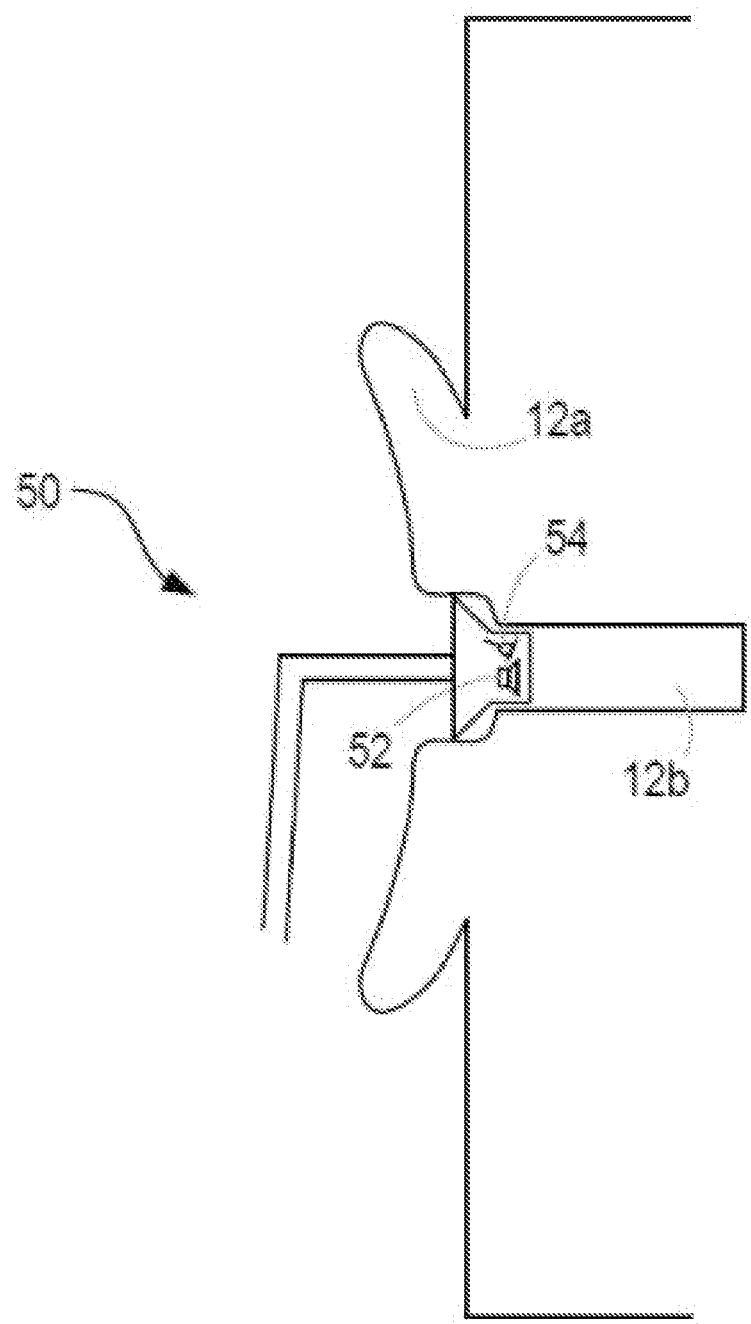

FIG 1d shows a further alternative personal audio device 50, comprising an in-ear headphone (or earphone), insert headphone, or ear bud. This headphone is configured to be partially or totally inserted within the ear canal 12b and may provide a relatively tight seal between the ear canal 12b and the external environment (i.e. it may be acoustically closed or sealed). The headphone may comprise one or more loudspeakers 52 and one or more microphones 54, as with the other devices described above, and these components may form part of an active noise cancellation system.

As the in-ear headphone may provide a relatively tight acoustic seal around the ear canal 12b, external noise (i.e. coming from the environment outside) detected by the microphone 54 is likely to be low.

Figure 1E:
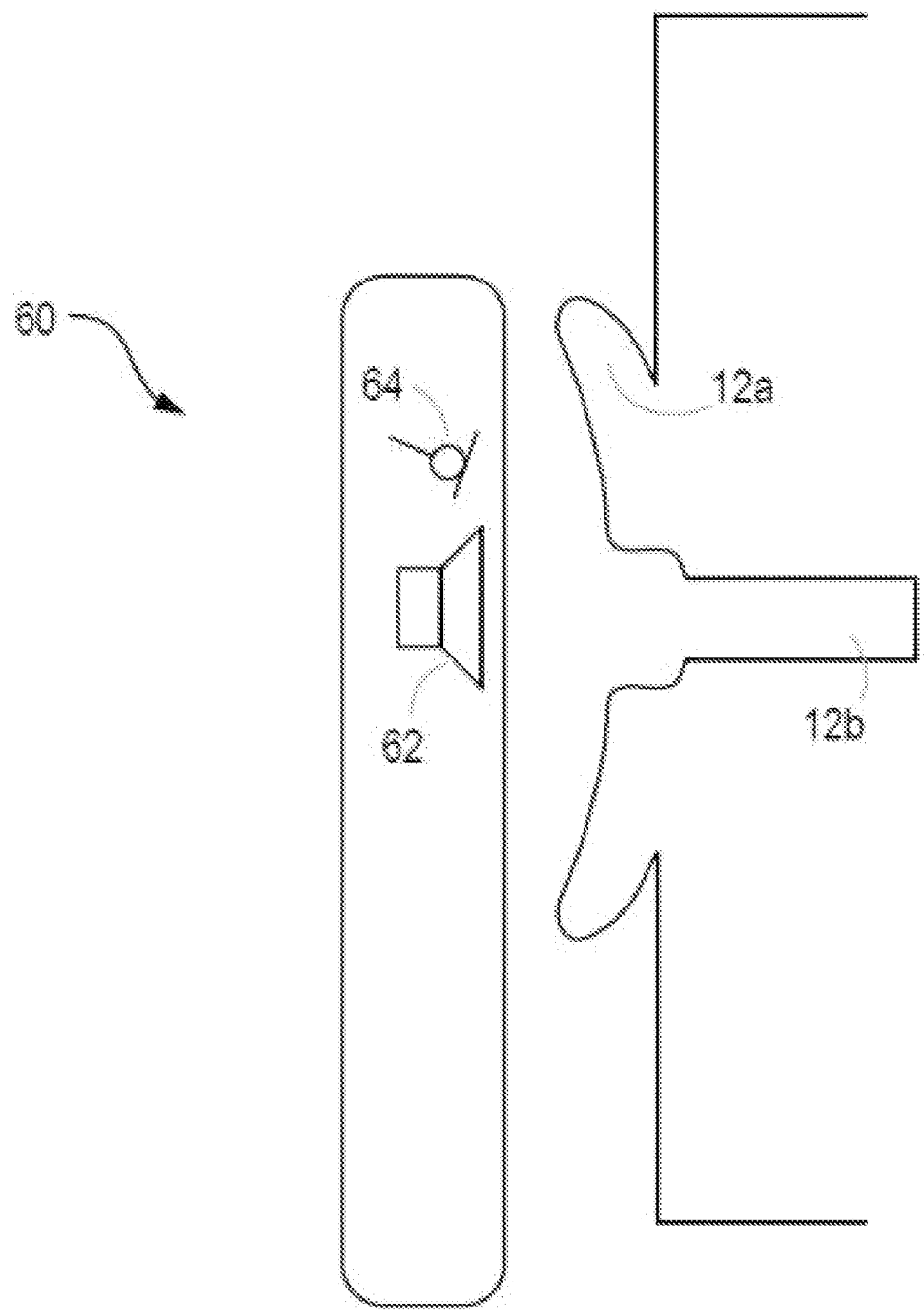

FIG. 1e shows a further alternative personal audio device 60, which is a mobile or cellular phone or handset. The handset 60 comprises one or more loudspeakers 62 for audio playback to the user, and one or more microphones 64 which are similarly positioned.

In use, the handset 60 is held close to the user's ear so as to provide audio playback (e.g. during a call). While a tight acoustic seal is not achieved between the handset 60 and the user's ear, the handset 60 is typically held close enough that an acoustic stimulus applied to the ear via the one or more loudspeakers 62 generates a response from the ear which can be detected by the one or more microphones 64. As with the other devices, the loudspeaker(s) 62 and microphone(s) 64 may form part of an active noise cancellation system.

All of the personal audio devices described above thus provide audio playback to a single user in use. Each device comprises one or more loudspeakers and one or more microphones, which may be utilized to generate biometric data related to the frequency response of the user's ear. The loudspeaker is operable to generate an acoustic stimulus, or acoustic probing wave, towards the user's ear, and the microphone is operable to detect and measure a response of the user's ear to the acoustic stimulus, e.g. to measure acoustic waves reflected from the ear canal or the pinna. The acoustic stimulus may be sonic (for example in the audio frequency range of say 20 Hz to 20 kHz) or ultra-sonic (for example greater than 20 kHz or in the range 20 kHz to 50 kHz) or near-ultrasonic (for example in the range 15 kHz to 25 kHz) or subsonic in frequency. In some examples the microphone signal may be processed to measure received signals of the same frequency as that transmitted.

Another biometric marker may comprise otoacoustic noises emitted by the cochlear in response to the acoustic stimulus waveform. The otoacoustic response may comprise a mix of the frequencies in the input waveform. For example, if the input acoustic stimulus consists of two tones at frequencies f1 and f2, the otoacoustic emission may include a component at frequency 2*f1-f2. The relative power of frequency components of the emitted waveform has been shown to be a useful biometric indicator. In some examples therefore the acoustic stimulus may comprise tones of two or more frequencies and the amplitude of mixing products at sums or differences of integer-multiple frequencies generated by otoacoustic emissions from the cochlear may be measured. Alternatively, otoacoustic emissions may be stimulated and measured by using stimulus waveforms comprising fast transients, e.g. clicks.

Depending on the construction and usage of the personal audio device, the measured response may comprise user-specific components, i.e. biometric data relating to the auricle 12a, the ear canal 12b, or a combination of both the auricle 12a and the ear canal 12b. For example, the circum-aural headphones shown in FIG. 1a will generally acquire data relating to the auricle 12a and potentially also the ear canal 12b. The insert headphones shown in FIG. 1d will generally acquire data relating only to the ear canal 12b.

One or more of the personal audio devices described above (or rather, the microphones within those devices) may be operable to detect bone-conducted voice signals from the user. That is, as the user speaks, sound is projected away from the user's mouth through the air. However, acoustic vibrations will also be carried through part of the user's skeleton or skull, such as the jawbone. These vibrations may be coupled to the ear canal 12b through the jaw or some other part of the user's skeleton or skull and detected by the microphone. Lower frequency sounds tend to experience a stronger coupling than higher frequency sounds, and voiced speech (i.e. that speech or those phonemes generated while the vocal cords are vibrating) is coupled more strongly via bone conduction than unvoiced speech (i.e. that speech or those phonemes generated while the vocal cords are not vibrating). The in-ear headphone 50 may be particularly suited to detecting bone-conducted speech owing to the tight acoustic coupling around the ear canal 12b.

All of the devices shown in FIGS. 1a to 1e and described above may be used to implement aspects of the disclosure.

Figure 2:
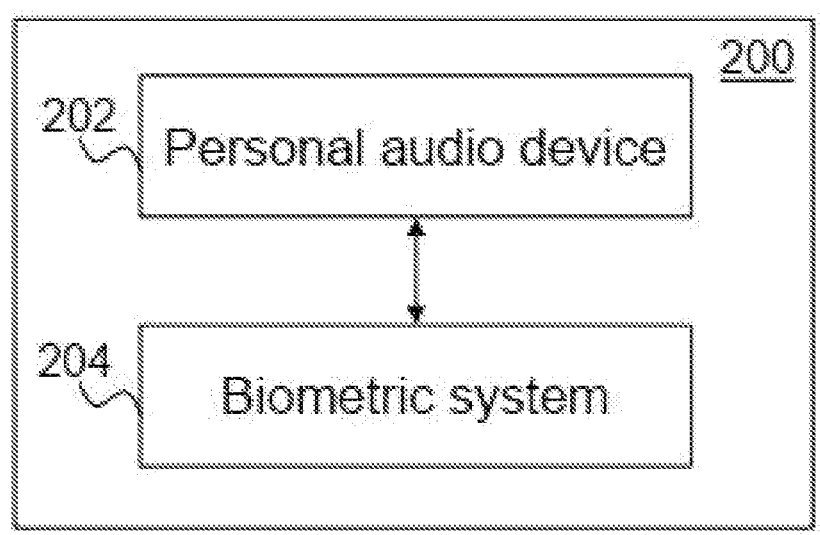
FIG. 2 shows an arrangement according to embodiments of the disclosure.

FIG. 2 shows an arrangement 200 according to embodiments of the disclosure. The arrangement 200 comprises a personal audio device 202 and a biometric system 204. The personal audio device 202 may be any device which is suitable for, or configurable to provide audio playback to a single user. The personal audio device 202 generally comprises one or more loudspeakers, and one or more microphones which, in use, are positioned adjacent to or within a user's ear. The personal audio device 202 may be wearable and comprise headphones for each of the user's ears. Alternatively, the personal audio device 202 may be operable to be carried by the user and held adjacent to the user's ear or ears during use. The personal audio device 202 may comprise headphones or a mobile phone handset, as described above with respect to any of FIGS. 1a to 1e.

The biometric system 204 is coupled to the personal audio device 202 and operative to control the personal audio device 202 to acquire biometric data which is indicative of the individual using the personal audio device 202.

The personal audio device 202 thus generates an acoustic stimulus for application to the user's ear and detects or measures the response of the ear to the acoustic stimulus. For example, the acoustic stimulus may be in the sonic range, or ultra-sonic range. In some embodiments, the acoustic stimulus may have a flat frequency spectrum over a relevant frequency range or be pre-processed in such a way that those frequencies that allow for a good discrimination between individuals are emphasized (i.e. have a higher amplitude than other frequencies). The measured response corresponds to the reflected signal received at the one or more microphones, with certain frequencies being reflected at higher amplitudes than other frequencies owing to the particular response of the user's ear.

The biometric system 204 may send suitable control signals to the personal audio device 202, so as to initiate the acquisition of biometric data, and receive data from the personal audio device 202 corresponding to the measured response. The biometric system 204 is operable to extract one or more features from the measured response and utilize those features as part of a biometric process.

Some examples of suitable biometric processes include biometric enrolment and biometric authentication. Enrolment comprises the acquisition and storage of biometric data which is characteristic of an individual. In the present context, such stored data may be known as an "ear print". Authentication (sometimes referred to as verification) comprises the acquisition of biometric data from an individual, and the comparison of that data to the stored ear prints of one or more enrolled or authorised users. A positive comparison (i.e. a determination that the acquired data matches or is sufficiently close to a stored ear print) results in the individual being authenticated. For example, the individual may be permitted to carry out a restricted action, or granted access to a restricted area or device. A negative comparison (i.e. a determination that the acquired data does not match or is not sufficiently close to a stored ear print) results in the individual not being authenticated. For example, the individual may not be permitted to carry out the restricted action or granted access to the restricted area or device.

According to embodiments of the disclosure, the personal audio device 202 is further operable to determine whether a signal to noise ratio (SNR) of the response signal is adequate for performing a biometric process, such as feature extraction for authentication. In response to determining that the SNR of the response signal is inadequate, the personal audio device 202 may be operable to modify one or more properties of the acoustic stimulus to improve the SNR of the response signal, as discussed in more detail below.

The biometric system 204 may, in some embodiments, form part of the personal audio device 202 itself. Alternatively, the biometric system 204 may form part of an electronic host device (e.g. an audio player) to which the personal audio device 202 is coupled, through wires or wirelessly. In yet further embodiments, operations of the biometric system 204 may be distributed between circuitry in the personal audio device 202 and the electronic host device.

Figure 3:
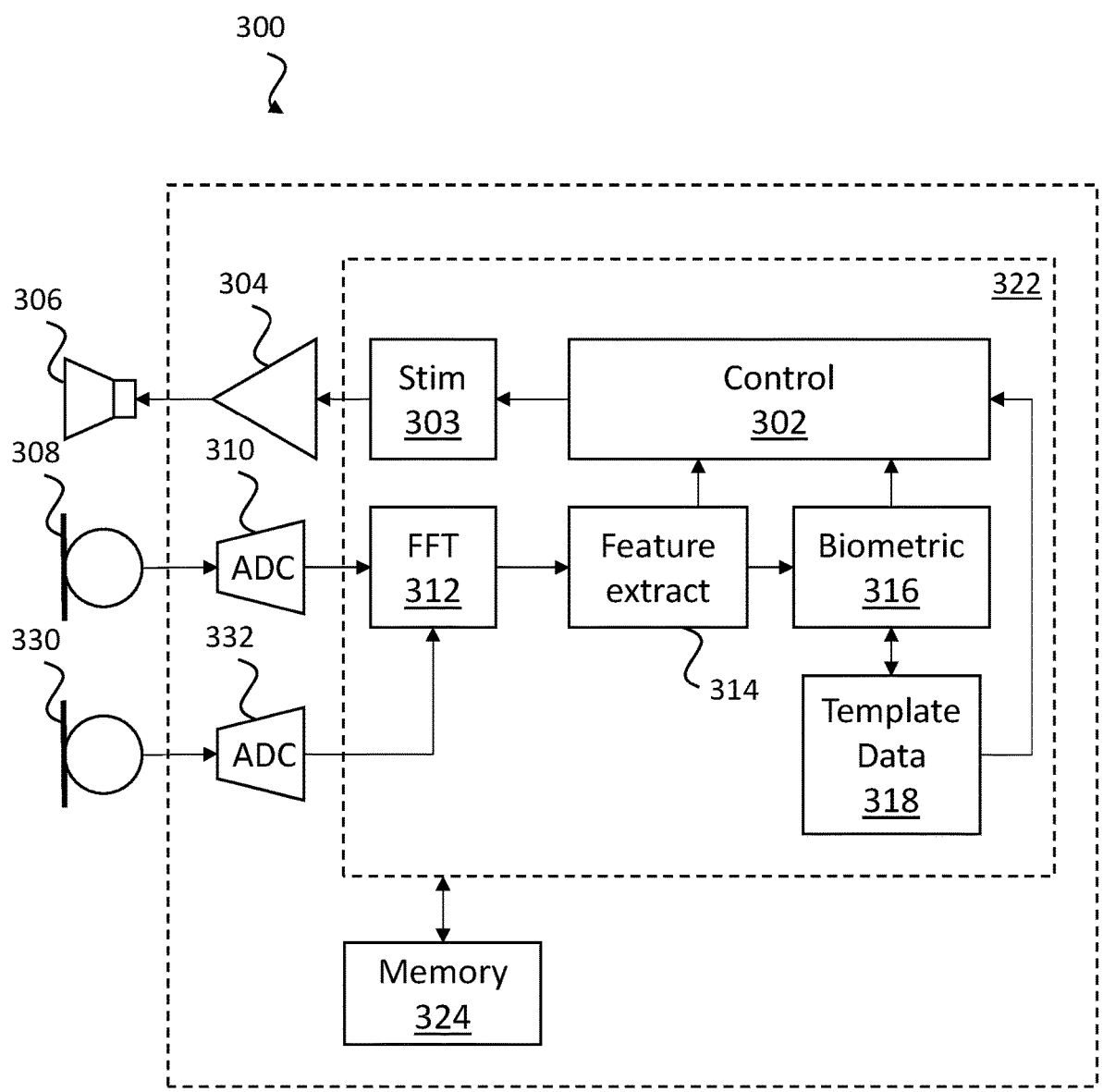
FIG. 3 shows a system according to embodiments of the disclosure.

FIG. 3 shows a system 300 according to embodiments of the disclosure.

The system 300 comprises processing circuitry 322, which may comprise one or more processors, such as a central processing unit or an applications processor (AP), or a digital signal processor (DSP).

The one or more processors may perform methods as described herein on the basis of data and program instructions stored in memory 324. Memory 324 may be provided as a single component or as multiple components or co-integrated with at least some of processing circuitry 322. Specifically, the methods described herein can be performed in processing circuitry 322 by executing instructions that are stored in non-transient form in the memory 324, with the program instructions being stored either during manufacture of the system 300 or personal audio device 202 or by upload while the system or device is in use.

The processing circuitry 322 comprises a stimulus generator module 303 which is coupled directly or indirectly to an amplifier 304, which in turn is coupled to a loudspeaker 306.

The stimulus generator module 303 generates an electrical audio signal and provides the electrical audio signal to the amplifier 304, which amplifies it and provides the amplified signal to the loudspeaker 306. The loudspeaker 306 generates a corresponding acoustic signal which is output to the user's ear (or ears). The audio signal may be sonic or ultra-sonic, for example. The audio signal may have a flat frequency spectrum or be pre-processed in such a way that those frequencies that allow for a good discrimination between individuals are emphasized (i.e. have a higher amplitude than other frequencies).

As noted above, the audio signal may be output to all or a part of the user's ear (i.e. the auricle 12a or the ear canal 12b). The audio signal is reflected off the ear, and the reflected signal (or echo signal) is detected and received by a microphone 308. The reflected signal thus comprises data, which is characteristic of the individual's ear, and suitable for use as a biometric.

The reflected signal is passed from the microphone 308 to an analogue-to-digital converter (ADC) 310, where it is converted from the analogue domain to the digital domain. Of course, in alternative embodiments the microphone 308 may be a digital microphone and produce a digital data signal (which does not therefore require conversion to the digital domain).

The signal is detected by the microphone 308 in the time domain. The features extracted for the purposes of the biometric process may be in the time domain. However, in some embodiments, the features extracted for the purposes of the biometric process may be in the frequency domain (in that it is the frequency response of the user's ear which is characteristic). The system 300 may therefore comprise a Fourier transform module 312, which converts the reflected signal to the frequency domain. For example, the Fourier transform module 312 may implement a fast Fourier transform (FFT).

The system 300 may further comprise an additional microphone 330, and an associated analogue-to-digital converter (ADC) 332 where necessary. The microphone 330 may be an external or out-of-ear microphone, which may be used for noise signal determinations, for example, as discussed in more detail below. An electrical audio signal generated by the additional microphone 330 may be provided (optionally via the ADC 332) to the FFT module 312 or to another FFT module (not shown). Equally, the electrical audio signal may be provided directly to the control module 302 in other embodiments.

The transformed signal from the microphone 308 is then passed to a feature extract module 314, which extracts one or more features of the transformed signal for use in a biometric process (e.g. biometric enrolment, biometric authentication, etc). For example, the feature extract module 314 may extract the resonant frequency of the user's ear. For example, the feature extract module 314 may extract one or more mel frequency cepstrum coefficients. Alternatively, the feature extract module 314 may determine the frequency response of the user's ear at one or more predetermined frequencies, or across one or more ranges of frequencies.

The extracted feature(s) are passed to a biometric module 316, which performs a biometric process on them. For example, the biometric module 316 may perform a biometric enrolment, in which the extracted features (or parameters derived therefrom) are stored as part of biometric template data 318 which is characteristic of the individual (i.e. as an ear print). The biometric template data 318 may be stored within the system 300 or remote from the system 300 (and accessible securely by the biometric module 316). In another example, the biometric 316 may perform a biometric authentication, and compare the one or more extract features to corresponding features stored in the biometric template data 318 (or multiple stored template ear prints). The biometric template data 318 may comprise template data, representations or ear prints of enrolled users. Additionally or alternatively the biometric template data 318 may comprise data representing multiple users, for example a subset of the general population. This template data 318 may also be accessible by the control module 302 for use in generating an acoustic stimulus as is described in more detail below.

The biometric module 316 may generate a biometric result (which may be the successful or unsuccessful generation of an ear print, as well as successful or unsuccessful authentication) and outputs the result to control module 302.

Thus in some embodiments the feature extract module 314 may be designed with foreknowledge of the nature of the stimulus, for example knowing the spectrum of the applied stimulus signal, so that the response or transfer function may be appropriately normalised. In other embodiments the feature extract module 314 may comprise a second input (not shown) to monitor the stimulus and hence provide the feature extract module 314 with information about the stimulus signal or its spectrum so that the feature extract module 314 may calculate the transfer function from the stimulus waveform stimulus to received acoustic waveform from which it may derive the desired feature parameters. In the latter case, the stimulus signal may also pass to the feature extract module 314 via the FFT module 312.

It has been found that the above process operates efficiently when environmental noise in the vicinity of the microphone 308 and the ear of the user is absent or low. However, as the level of environmental noise increases, the response to the acoustic stimulus measured by the microphone 308, becomes increasingly corrupted. This lack of robustness leads to errors and uncertainty in the biometric result generated by the system 300. It has also been found that different types of environmental noise corrupt the measured response to different degrees.

Figure 4:
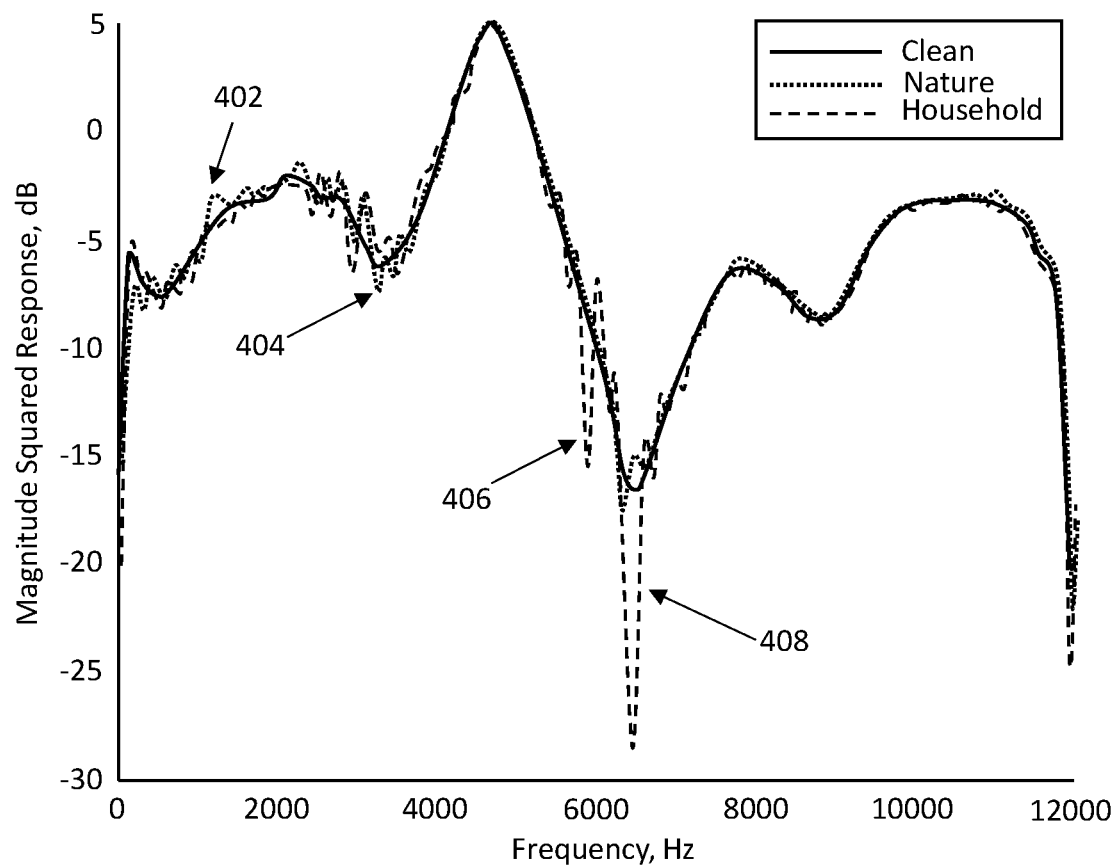
FIG. 4 graphically illustrates a measured frequency response of an ear canal to an acoustic probe in the presence and absence of noise.

FIG. 4 is a graph of the measured frequency response of the ear canal of a user in the presence of no noise (clean), natural noise (nature), and household noise (household). The presence of both natural and household noise leads to spurious spectral artefacts 402, 404, 406, 408 in the measured frequency response. It can also be seen that the artefacts 406, 408 present in the frequency response measured in the presence of household noise are more pronounced than those artefacts 402, 404 present in the frequency response measured in the presence of the noise of nature.

Figure 5:
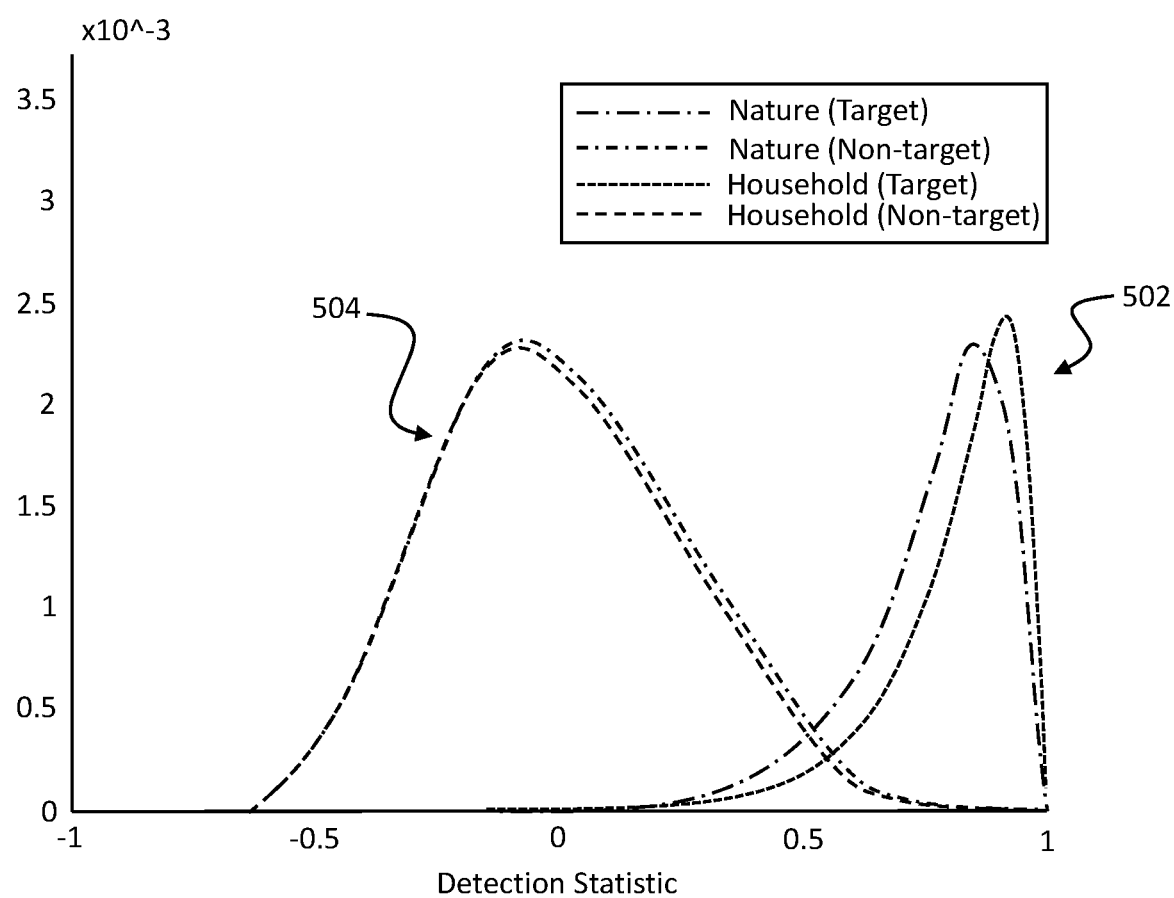
FIGS. 5 is a graph showing probability distribution functions for detection statistics representing similarities between ear canal responses and stored templates.

FIG. 5 is a graph showing probability density functions of detection statistics for an enrolled user 502 and an imposter 504 in two different noise conditions. The detection statistic (x-axis) represents the similarity between the ear canal response estimated from the received audio signal and stored template data 318. A statistic of 1 means that a measured response is identical to a stored template.

It can be seen that the detection statistic value is substantially higher for the enrolled user 502 than the imposter 504. To achieve good authentication performance, the detection statistic distribution for the enrolled user 502 and the imposter 504 should be well separated. This ensures that a threshold can be set (substantially between the enrolled and imposter detection statistics) that minimizes false rejection of enrolled users whilst also minimising false acceptance of imposters.

In the example shown in FIG. 5, in the presence of natural noise, the detection statistic distribution for the enrolled user overlaps to a greater extent with the imposter distribution when compared to similar distributions in the presence of household noise. This may result in reduced authentication performance, for example for a fixed false accept rate (FAR). It is preferable that the distribution is invariant to different noise types such that a single threshold can be set that improves the likelihood of similar authentication performance for different noise types.

Thus, it can be seen that noise present in estimated system responses, such as an ear canal impulse response (ECIR), can result in noise dependent authentication performance variation.

Embodiments of the present disclosure aim to address or at least ameliorate problems associated with the corruption of estimations of ear canal impulse and frequency response by additive noise. In embodiments of the present disclosure, probe signals applied to systems such as an ear canal may be adapted such that their application to the ear canal leads to whitening of the environmental noise picked up during estimation of the ear canal response to the probe signal. In some embodiments, a fixed probe signal is adaptively filtered based on an estimate of the environmental noise affecting the ear canal (or other system under test). A filter characteristic of the filter used to adapt the fixed probe signal may be generated based on a prevailing noise condition. This condition may be measured at one or more transducers proximate the system under test (e.g., the ear canal). By whitening noise present in the estimate of the system response to the probe signal, through appropriate adaptation of the probe signal, such noise may be substantially regularized. This in turn leads to improvements in the robustness of authenticating the identity of the system, such as the characteristic of an ear canal (or other system) under test.

In addition, embodiments of the present disclosure provide noise-robust methods of feature extraction in which resonant and anti-resonant regions of a system response are parametrically modelled. Useful features may be extracted by parametric models and the model parameters augmented with the estimated system impulse response. The resultant extracted feature sets, which include parametrically modelled parameters, tend to be more robust to different noise conditions as well as different noise types.

In some embodiments, synergy may be achieved by combining the whitening of noise in system estimates with parametric feature extraction. This is because whitened noise in the measured system response may be substantially removed in subsequent parametric feature extraction.

Taking the above into consideration, in the example of ear biometrics, the control module 302 may be configured to control the stimulus generator module 303 to generate an acoustic stimulus having the properties described above.

Figure 6:
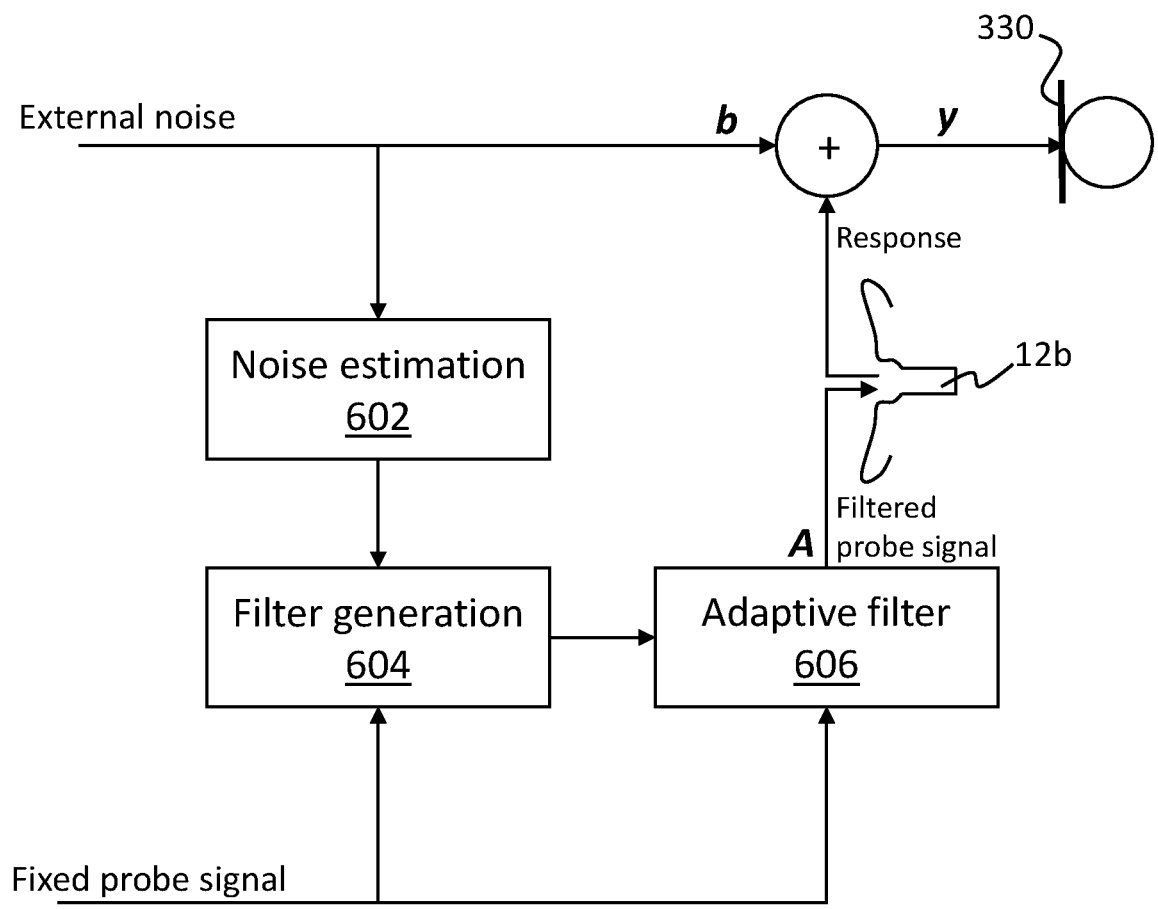
FIG. 6 is a block diagram of a process which may be implemented by the system shown in FIG. 3.

FIG. 6 is a block diagram of a process 600 which may be implemented by the processing circuitry 322 for generating a probe signal or stimulus having the characteristics described above. For context, the process 600 is described below as being implemented by the system 300 shown in FIG. 3. In other embodiments, however, the process 600 may be implemented in another system (not shown) which may be proximate to or remote from the system 300. For example, one or more steps in the process 600 may be implemented in the cloud. The generated acoustic stimulus may be used by the system 300 or other systems for use in a biometric process, such as biometric enrolment or authentication, an example of which is described above. For example, where a user has multiple personal audio devices, the acoustic stimulus by the process 600 may be utilised by each of those devices for one or more biometric processes. Various steps of the process 600 described below may be implemented by different modules of the system 300 or other systems which may themselves be disparate from one another.

It will be understood that when a probe signal A is applied to the ear canal 12b of a user, the signal y measured at the microphone 330 of the system 300 comprises both external noise and the response to the probe signal A. The signal y may be defined as follows:

$y = Ah + b$

Where h is the response of the ear canal.

A least square estimate of h may be given by the following equation.

$$\hat{h} = (A^T A)^{-1} A^T y$$
$$= (A^T A)^{-1} A^T A h + (A^T A)^{-1} A^T b$$
$$= hest + Wb$$

Where:

$hest = (A^T A)^{-1} A^T A h$ $Wb = (A^T A)^{-1} A^T b$

Hence, the least square estimate of the canal response h is corrupted by additive noise Wb.

Taking the above into account, the process 600 aims to whiten the additive noise Wb so as to remove or reduce its variance with respect to time (i.e., regularizing the additive noise). In doing so, subsequent processing of the signal y received at the microphone 300 can more easily remove the noise. The effect of the whitened noise on the authentication performance can be minimized by using parametric modelling. Model parameters may be further expanded to derive features. The combined regularization of noise in the measured system response on the one hand and parametric modelling on the other hand, leads to improved authentication performance.

Referring to FIG. 6, at step 602, the processing circuitry 322 may obtain an estimate of the external or environmental noise b present in the ear canal. In some embodiments, this noise estimate may be obtained by sampling the microphone 308 which may be located proximate the ear canal. It is preferable that any such sample is obtained during periods in which no sound is being produced by the loudspeaker 306 to minimize interference with the measured noise. In other embodiments, the noise estimate may be obtained by comparing the signal received at the microphone 308 with a signal received at the additional microphone 330 which is external to the personal audio device. For example, a transfer function between the microphone 308 and the additional microphone 330 may be estimated. This transfer function may then be used to generate an estimate of the environmental noise b at microphone 308 by filtering the microphone 330 signal with the estimated transfer function.

At step 604 a set of filter parameters may be generated based on the estimated noise b and the fixed (unfiltered) probe signal. The filter parameters may be continuously or periodically updated based on the noise estimate b.

The filter parameters may be chosen so as to whiten the noise component Wb as estimated using least squared estimation, i.e.:

$Wb = (A^T A)^{-1} A^T b$

Specifically, filter parameters are chosen to produce a probe signal A which, in combination with the noise estimate b leads to the expression $(A^T A)^{-1} A^T b$ resembling white noise or near-white noise (or in other words having a flat or near flat frequency response). In another embodiment, characteristics of the whitening filter are derived by performing spectral analysis on the filtered noise estimate $(A^T A)^{-1} A^T b$ to generate a spectral estimate. The whitening filter may be designed to have a transfer function which approximates the inverse of the spectral estimate. For example, low order linear prediction analysis may be performed and the all-pole LPC model coefficients may be used as inputs to the whitening filter.

The filter parameters may then be used at step 606 to augment the fixed probe signal and generate a filtered probe signal A for application to the ear canal 12b. Whilst in the embodiment shown in FIG. 6 a fixed probe signal is adapted using an adaptive filter, in other embodiments the probe signal A may be generated from scratch based on the noise estimation b.

Figure 7:
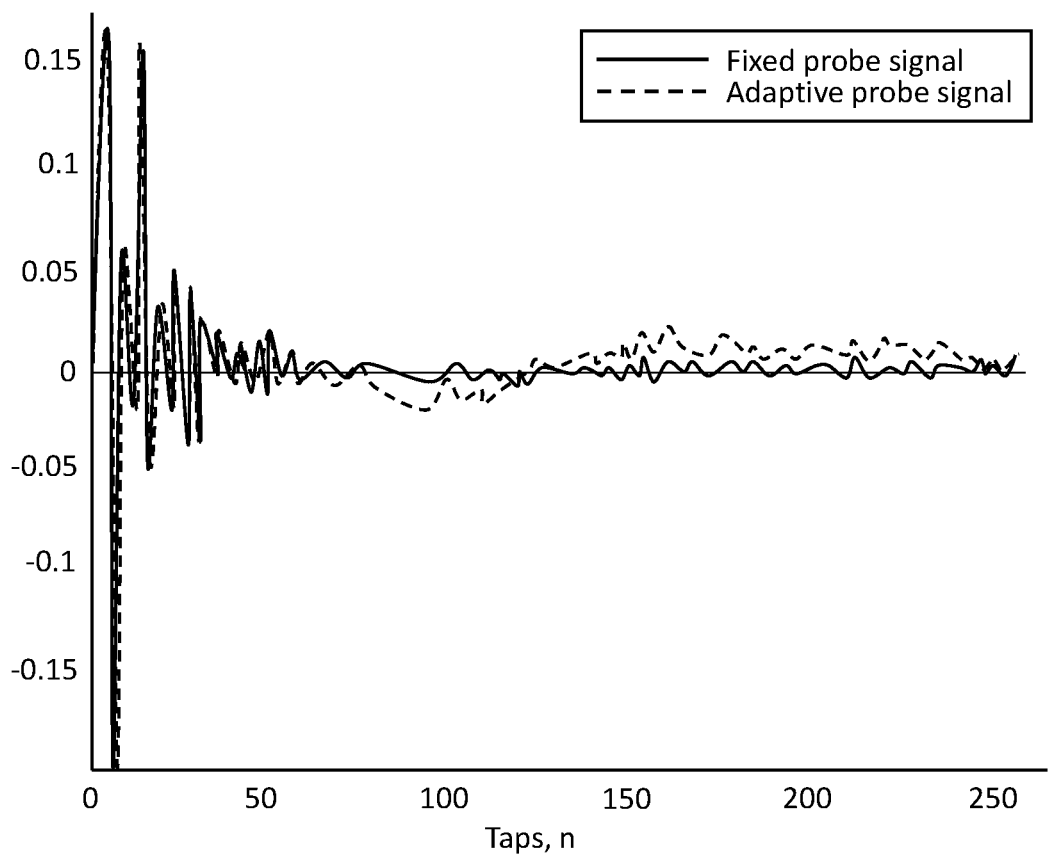
FIG. 7 is a graph comparing measured ear canal impulse responses in response to different probe signals.

FIG. 7 is a graph comparing the measured ear canal impulse response to a fixed probe signal and to a probe signal adapted to whiten environmental noise present at the ear canal. It can be seen that whilst noise is still present in the measured impulse response to the adaptive probe signal, the noise is less fluctuating over time.

Figure 8:
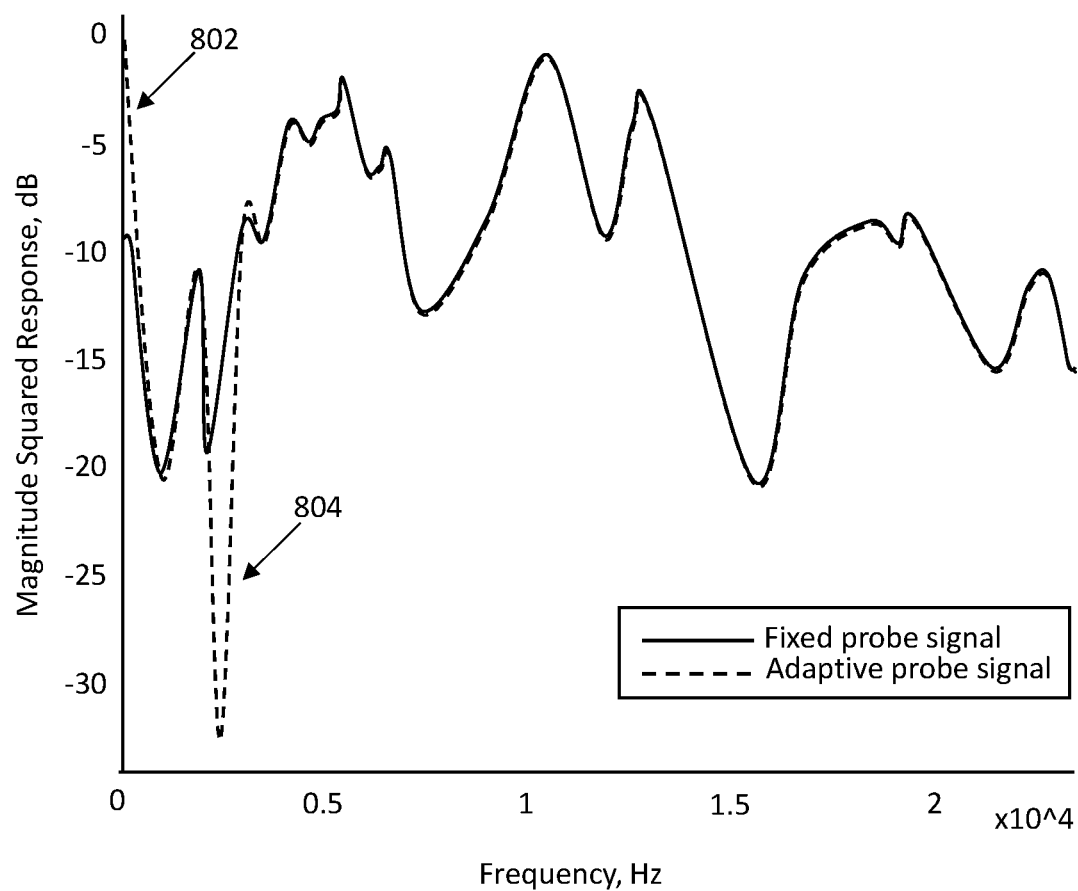
FIG. 8 is a graph comparing measured ear canal frequency responses in response to different probe signals.

FIG. 8 shows the corresponding ear canal frequency response to the same fixed probe signal and the same adaptive probe signal. It can be seen that spurious errors 802, 804 due to environmental noise which are present in the frequency response to the fixed probe signal are not present in the response to the adaptive probe signal. Thus, the augmented probe signal acts to remove spurious errors associated with environmental noise present during measurements of ear canal response.

Various method exist for processing system responses, such as ear canal impulse and frequency responses to remove noise. The inventors have found that parametric modelling is particularly effective in extracting features from system responses comprising time-invariant noise (such as the ear canal response measured in response to the adapted probe signal described above).

Figure 9:
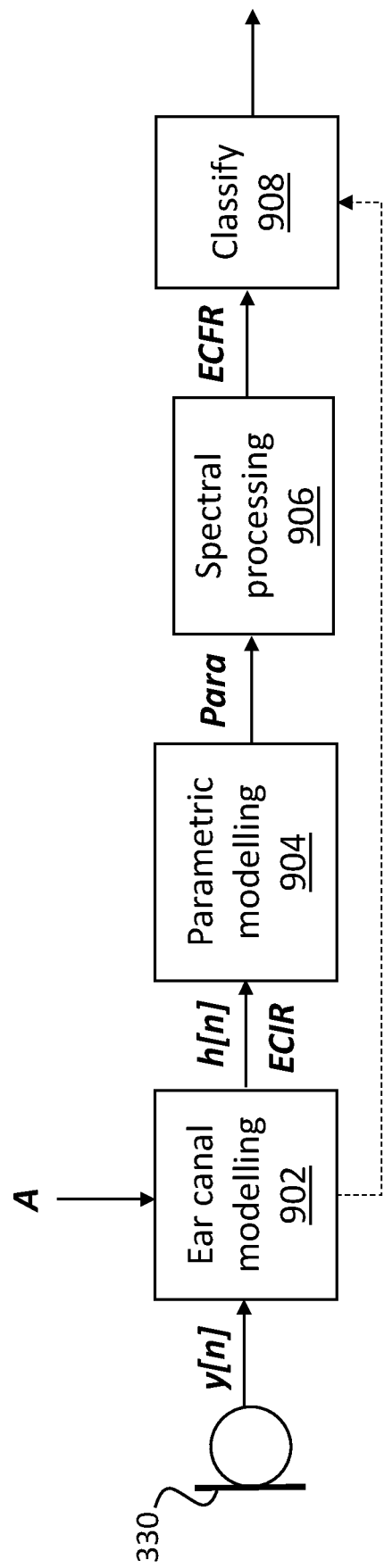
FIG. 9 is a block diagram of a process which may be implemented by the system shown in FIG. 3.

FIG. 9 is a block diagram of a process 900 which may be implemented by the processing circuitry 322 for processing a system response, such as an ear canal impulse response measured at the transducer 308 of the system 300.

At step 902, an initial ear canal impulse response ECIR is estimated using conventional correlation techniques known in the art. Example techniques include least mean squares (LMS), least squares, and recursive least squares (RLS). The ECIR may be estimated using an ear canal model based on the received audio signal y[n] from the transducer 330 and the probe signal A applied to the ear canal.

At step 904, parametric modelling may be performed on the estimated ECIR h[n] to refine the estimate. A parametric representation Para of the ECIR h[f] is generated at this step. Such modelling may comprise using linear predictive coding (LPC) in some embodiments. In some embodiments, an all pole model may be used to model the parameters based on the estimated ECIR. Additionally or alternatively, a pole-zero model may be used. To derive pole-zero modelling parameters, Padé approximation or Prony's method may be used.

The parametric representation captures correlated information in the ear canal response, such as resonance or anti-resonance. Such information is exemplified by peaks and troughs in the frequency response curves shown in FIGS. 4 and 8.

The parametric representation Para may comprise parameters which may then be used to generate a frequency spectrum or ECFR. Thus, at step 906 spectral processing may be performed to generate such a frequency spectrum.

Where the parametric representation Para is generated using linear prediction, the Nth order LPC model frequency spectrum can be written as:

$$H_{LP}^{ECIR}(z) = \frac{1}{1 + \sum_{k=1}^{N} a_k z^{-k}}$$

Where $a_k$ is a parameter of the parametric representation Para calculated during the parametric modelling 904.

Where the parametric representation Para is generated using pole-zero modelling, the pole-zero model frequency spectrum can be written as:

$$H_{PZ}^{ECIR}(z) = \frac{\sum_{k=0}^{M} b_m z^{-m}}{1 + \sum_{k=1}^{N} a_k z^{-k}}$$

Where $a_k$ and $b_m$ are parameters of the parametric representation Para calculated during the parametric modelling 904.

The resultant spectral representation obtained from spectral processing of the parametric model parameters output at step 906 has a smoother spectrum whilst providing robustness to noise. This in turn leads to more accurate verification/authentication. Further, when coupled with the techniques described above for probe signal generation, the estimate of ECIR is even more robust when compared to using conventional classification techniques with an adaptive probe signal. This is because the frequency spectrum of the ear canal response will be substantially absent of or have reduced additive modelling error since the modelling error due to the additive noise has been whitened (i.e. temporally uncorrelated).

Optionally, in addition to generating a frequency spectrum of the ear canal response, e.g., the ECFR of the system, the spectral processing at step 906 may include feature extraction. Such feature extraction may be performed by the feature extract module 314. One or more features of the spectrum may be extracted. Such extraction may be performed for use in a biometric process (e.g. biometric enrolment, biometric authentication, etc). For example, the feature extract module 314 may extract the resonance or antiresonance of the system (e.g. peaks and troughs). For example, the feature extract module 314 may extract one or more mel frequency cepstrum coefficients. Additionally or alternatively, the feature extract module 314 may determine the frequency response of the user's ear at one or more predetermined frequencies, or across one or more ranges of frequencies.

At step 908, the spectrum and/or the one or more extracted features may then be classified. For example, the spectrum and/or the one or more extracted features may be compared with a stored authentication template, such as the template data 318. A determination as to whether the modelled system (e.g. ear canal) is authenticated may then depend on a similarity between the stored template and the parametric representation.

Optionally, the estimated ECIR may be combined with the spectrum and/or one or more extracted features for use during classification, as denoted by the broken line in FIG. 9 to further improve performance of the process 900.

As discussed throughout the present disclosure, whilst the examples described herein in relation to the ear canal, the present disclosure is not limited to such systems. The concepts described herein can be applied to any system which is subject to externally applied noise and which have an unknown transfer function. For example, embodiments of the present disclosure may equally be applied to account for environmental noise present during active noise cancellation in a personal audio device, such as those described above.

The skilled person will recognise that some aspects of the above-described apparatus and methods may be embodied as processor control code, for example on a non-volatile carrier medium such as a disk, CD- or DVD-ROM, programmed memory such as read only memory (Firmware), or on a data carrier such as an optical or electrical signal carrier. For many applications embodiments of the invention will be implemented on a DSP (Digital Signal Processor), ASIC (Application Specific Integrated Circuit) or FPGA (Field Programmable Gate Array). Thus the code may comprise conventional program code or microcode or, for example code for setting up or controlling an ASIC or FPGA. The code may also comprise code for dynamically configuring re-configurable apparatus such as re-programmable logic gate arrays. Similarly the code may comprise code for a hardware description language such as Verilog™ or VHDL (Very high speed integrated circuit Hardware Description Language). As the skilled person will appreciate, the code may be distributed between a plurality of coupled components in communication with one another. Where appropriate, the embodiments may also be implemented using code running on a field-(re)programmable analogue array or similar device in order to configure analogue hardware.

Note that as used herein the term module shall be used to refer to a functional unit or block which may be implemented at least partly by dedicated hardware components such as custom defined circuitry and/or at least partly be implemented by one or more software processors or appropriate code running on a suitable general purpose processor or the like. A module may itself comprise other modules or functional units. A module may be provided by multiple components or sub-modules which need not be co-located and could be provided on different integrated circuits and/or running on different processors.

Embodiments may be implemented in a host device, especially a portable and/or battery powered host device such as a mobile computing device for example a laptop or tablet computer, a games console, a remote control device, a home automation controller or a domestic appliance including a domestic temperature or lighting control system, a toy, a machine such as a robot, an audio player, a video player, or a mobile telephone for example a smartphone.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

It should be noted that the above-mentioned embodiments illustrate rather than limit the invention, and that those skilled in the art will be able to design many alternative embodiments without departing from the scope of the appended claims. The word "comprising" does not exclude the presence of elements or steps other than those listed in a claim, "a" or "an" does not exclude a plurality, and a single feature or other unit may fulfil the functions of several units recited in the claims. Any reference numerals or labels in the claims shall not be construed so as to limit their scope.

As used herein, when two or more elements are referred to as "coupled" to one another, such term indicates that such two or more elements are in electronic communication or mechanical communication, as applicable, whether connected indirectly or directly, with or without intervening elements.

This disclosure encompasses all changes, substitutions, variations, alterations, and modifications to the example embodiments herein that a person having ordinary skill in the art would comprehend. Similarly, where appropriate, the appended claims encompass all changes, substitutions, variations, alterations, and modifications to the example embodiments herein that a person having ordinary skill in the art would comprehend. Moreover, reference in the appended claims to an apparatus or system or a component of an apparatus or system being adapted to, arranged to, capable of, configured to, enabled to, operable to, or operative to perform a particular function encompasses that apparatus, system, or component, whether or not it or that particular function is activated, turned on, or unlocked, as long as that apparatus, system, or component is so adapted, arranged, capable, configured, enabled, operable, or operative. Accordingly, modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Although exemplary embodiments are illustrated in the figures and described below, the principles of the present disclosure may be implemented using any number of techniques, whether currently known or not. The present disclosure should in no way be limited to the exemplary implementations and techniques illustrated in the drawings and described above.

Unless otherwise specifically noted, articles depicted in the drawings are not necessarily drawn to scale.

All examples and conditional language recited herein are intended for pedagogical objects to aid the reader in understanding the disclosure and the concepts contributed by the inventor to furthering the art, and are construed as being without limitation to such specifically recited examples and conditions. Although embodiments of the present disclosure have been described in detail, it should be understood that various changes, substitutions, and alterations could be made hereto without departing from the spirit and scope of the disclosure.

Although specific advantages have been enumerated above, various embodiments may include some, none, or all of the enumerated advantages. Additionally, other technical advantages may become readily apparent to one of ordinary skill in the art after review of the foregoing figures and description.

To aid the Patent Office and any readers of any patent issued on this application in interpreting the claims appended hereto, applicants wish to note that they do not intend any of the appended claims or claim elements to invoke 35 U.S.C. § 112(f) unless the words "means for" or "step for" are explicitly used in the particular claim.

The invention claimed is:

1. A method of identifying a system, the method comprising:
   obtaining an indication of background noise present at the system;
   generating a probe signal based on the indication;
   applying the probe signal to the system;
   estimating a response of the system to the probe signal; and
   identifying the system based on the measured response and the probe signal, wherein the probe signal comprises a whitening component configured to whiten noise in the estimated response due to the background noise present at the system.

2. The method of claim 1, wherein the probe signal is an acoustic stimulus for use in an acoustic process on a user and the system comprises an ear canal of the user.

3. The method of claim 2, wherein the acoustic process comprises active noise cancellation (ANC).

4. The method of claim 3, wherein the probe signal is an audio playback signal.

5. The method of claim 4, wherein the estimated response represents a combination of a leakage path around a personal audio device worn by the user and a response of the ear canal to probe signal.

6. The method of claim 4 wherein the estimated response is used to adapt the probe signal for the ANC.

7. The method of claim 6, wherein the ANC comprises feedback ANC or feedforward ANC or feedback ANC and feedforward ANC.

8. The method of claim 2, wherein the acoustic process comprises an ear biometric process.

9. The method of claim 8, wherein identifying the system comprises obtaining an ear canal response of the user's ear.

10. The method of claim 2, wherein the indication of background noise is obtained from an internal microphone of a personal audio device proximate the user's ear.

11. The method of claim 10, wherein the indication of background noise is obtained from the internal microphone and an external microphone of the personal audio device worn by the user.

12. The method of claim 11, wherein obtaining the indication of background noise comprises comparing an internal microphone signal from the internal microphone to an external microphone signal at the external microphone.

13. The method of claim 12, wherein obtaining the indication of background noise comprises:
   estimating a transfer function between the external microphone signal and internal microphone signal; and
   filtering the external microphone signal by the estimated transfer function.

14. The method of claim 1, wherein generating the probe signal comprises:
   adapting a fixed probe signal based on the indication of background noise.

15. The method of claim 14, wherein generating the probe signal comprises:
   determining filter parameters for whitening the noise in the measured response due to the background noise present at the system; and
   filtering the fixed probe signal using the filter parameters.

16. The method of claim 1, wherein identifying the system comprises:
   performing parametric modelling on the estimated response to generate a parametric representation of the estimated response.

17. The method of claim 16, wherein the parametric modelling comprising linear predictive coding (LPC).

18. The method of claim 16, wherein identifying the system comprises:
   estimating a frequency spectrum of the system response based on parametric representation; and
   comparing one or more features of the frequency spectrum with one or more templates.

19. The method of claim 18, wherein identifying the system comprises:
   generating an authentication result for each comparison between the one or more features and the one or more templates.

20. The method of claim 19, wherein the authentication result is generated by a machine learning classifier trained using the one or more templates.

21. The method of claim 18, further comprising comparing the measured response or the frequency spectrum with the one or more templates.

22. A method of authenticating a user as an authorised user, the method comprising:
   obtaining an indication of background noise present at an ear canal of the user;
   generating a probe signal based on the indication;
   applying the probe signal to the ear canal of the user;
   measuring sound proximate the ear canal during or after application of the probe signal;
   estimating a response of the ear canal to the probe signal based on the measured sound; and
   identifying the user based on the estimated response and the probe signal, wherein the probe signal comprises a whitening component configured to whiten the noise present in the estimated response due to the background noise present at the system.

23. A non-transitory machine-readable medium storing instructions which, when executed by one or more processors, cause an electronic apparatus to perform a method of identifying a system, the method comprising:
   obtaining an indication of background noise present at the system;
   generating a probe signal based on the indication;
   applying the probe signal to the system;
   estimating a response of the system to the probe signal; and
   identifying the system based on the measured response and the probe signal, wherein the probe signal comprises a whitening component configured to whiten noise in the estimated response due to the background noise present at the system.

24. An apparatus for identifying a system, the apparatus comprising:
  an input for obtaining an indication of background noise present at the system; and
  one or more processors configured to control the apparatus to:
    generate a probe signal based on the indication;
    apply the probe signal to the system;
  estimate a response of the system to the probe signal; and
  identify the system based on the measured response and the probe signal, wherein the probe signal comprises a whitening component configured to whiten noise in the estimated response due to the background noise present at the system.

25. An electronic device comprising the apparatus of claim 24.

26. An apparatus for identifying a user, the apparatus comprising:
  an input for obtaining an indication of background noise present at an ear canal of the user; and
  one or more processors configured to control the apparatus to:
    generate a probe signal based on the indication;
    apply the probe signal to the ear canal of the user;
    measure sound proximate the ear canal during or after application of the probe signal;
    estimate a response of the ear canal to the probe signal based on the measured sound; and
  identify the user based on the estimated response and the probe signal, wherein the probe signal comprises a whitening component configured to whiten the noise present in the estimated response due to the background noise present at the system.

* * * * *